United States Patent [19]

Guth

[11] Patent Number: 4,954,486
[45] Date of Patent: Sep. 4, 1990

[54] FUROSEMIDE AS TINNITUS SUPPRESSANT

[75] Inventor: Paul S. Guth, New Orleans, La.

[73] Assignee: Tulane Educational Fund, New Orleans, La.

[21] Appl. No.: 456,201

[22] Filed: Dec. 20, 1989

Related U.S. Application Data

[63] Continuation of Ser. No. 363,408, Jun. 7, 1989, abandoned, which is a continuation of Ser. No. 95,697, Sep. 14, 1987, abandoned, which is a continuation-in-part of Ser. No. 937,460, Dec. 2, 1986, Pat. No. 4,735,968, which is a continuation of Ser. No. 742,347, Jun. 5, 1985, abandoned.

[51] Int. Cl.$^5$ ............................................. A61K 31/635
[52] U.S. Cl. .................................................... 514/158
[58] Field of Search ......................... 514/155, 156, 158

[56] References Cited

U.S. PATENT DOCUMENTS 3,058,882  10/1662  Stürm et al. ........................ 514/156

Primary Examiner—Douglas W. Robinson
Assistant Examiner—Raymond J. Henley, III
Attorney, Agent, or Firm—Nixon & Vanderhye

[57] ABSTRACT

Tinnitus symptoms were treated with furosemide, a loop diuretic, and reductions in tinnitus symptoms were observed.

3 Claims, No Drawings

FUROSEMIDE AS TINNITUS SUPPRESSANT

This application is a continuation of application Ser. No. 07/363,408 filed June 7, 1989, now abandoned, which is a continuation of application Ser. No. 07/095,697 filed Sept. 14, 1987, now abandoned, which is a continuation-in-part of application Ser. No. 06/937,460 filed Dec. 2, 1986, now U.S. Pat. No. 4,735,968, which is a continuation of application Ser. No. 06/742,347, now abandoned.

This invention relates to a method of treating tinnitus in which an effective quantity of furosemide (4-chloro-N-furfuryl-5-sulfamoylanthranilic acid) is administered to a patient experiencing tinnitus and his/her symptoms are alleviated.

Tinnitus is the perception of sound in the absence of acoustic stimulus and may be of the buzzing, ringing, whistling or hissing quality, or it may involve more complex sounds that vary over time. Tinnitus may be intermittent ir continuous and an associated hearing loss may also be present. Tinnitus may occur as a symptom of nearly all ear disorders. The mechanism involved in the production of tinnitus has not previously been explained. Although no specific medical or surgical therapy is reported for tinnitus in *The Merck Manual*, 14th edition (1982), it is suggested that patients may find relief by playing background music to mask the tinnitus.

I have successfully used furosemide as a palliative in the treatment of human tinnitus. Furosemide, a loop diuretic acting on the loop of Henle in the kidney, is used for the treatment of edema and hypertension. Furosemide is the subject of U.S. Pat. No. 3,058,882, and is currently marketed in the United States as LASIX ® by Hoechst-Roussel in tablet and oral solution form (for oral use), and as a sterile solution (for injection). Other members of the loop diuretic group are ethacrymic acid (Merk Index, 10th edition, monograph 3664) and bumetanide (Merck Index, 10th edition, monograph 1452).

I have observed as a class the loop diuretics, in contradistinction to other diuretics, affect hearing by reducing the endocochlear potential. This potential must be maintained for proper function of the inner ear.

I have discovered, and hereby disclose, that the loop diuretics, particularly furosemide, are useful as a palliative in the treatment of human tinnitus.

The amount of furosemide administered and the dosage regime will be determined by the clinician. Being a known compound about which there is considerable clinical experience with known toxicology and pharmacokinetics, the limits of tolerance and toxicity are available as benchmarks for initial therapy. I have found amounts of furosemide in the range of 20 to 120 mg daily, preferably about 40 to 80 mg/day, in divided doses, to be effective in providing an acceptable degree of relief to patients suffering from tinnitus. Administration should preferably not be greater than 6 mg/kg body weight. Therapy may be continued solely as the tinnitus symptoms exist. Hearing is often restored to its previous level at the end of one week or less of treatment.

The route of administration may be one of convenience selected by the clinician; oral administration in the form of an oral dosage unit such as a tablet, capsule or liquid, is preferred, although intravenous administration may also be used.

The method of the present invention will be illustrated with reference to the following investigation.

EXAMPLE

A group of 9 patients, all diagnosed as having active tinnitus, were given furosemide (intravenously, 40 mg). Four of the 9 reported a reduction in their tinnitus.

What is claimed is:

1. A method of treating the symptoms of tinnitus in a person experiencing same comprising administering to said person a tinnitus-alleviating effective amount of furosemide.

2. The method as claimed in claim 1 in which the amount administered is in the range of from 20 to 120 mg/day.

3. The method as claimed in claim 2 in which the amount administered is in the range of from about 40 mg/day to about 80 mg/day.

* * * * *